United States Patent [19]

Brown

[11] Patent Number: 5,018,519
[45] Date of Patent: May 28, 1991

[54] MASK FOR ADMINSTERING AN ANESTHETIC GAS TO A PATIENT

[76] Inventor: Glenn E. Brown, 2831 Research Park Dr., Soquel, Calif. 95037

[21] Appl. No.: 562,242

[22] Filed: Aug. 3, 1990

[51] Int. Cl.⁵ .................................................. A61M 16/06
[52] U.S. Cl. .............................. 128/203.29; 128/205.25; 128/206.21; 128/206.28
[58] Field of Search ................. 128/205.25, 206.21, 128/206.26, 206.28, 207.12, 203.29

[56] References Cited

U.S. PATENT DOCUMENTS

| | | |
|---|---|---|
| 1,632,449 | 6/1927 | McKesson . |
| 2,888,012 | 5/1959 | Larson ............................ 128/207.12 |
| 3,395,701 | 8/1968 | Bartlett, Jr. et al. ............ 128/146.5 |
| 3,721,239 | 3/1973 | Myers ................................. 128/188 |
| 4,015,598 | 4/1977 | Brown ................................. 128/188 |
| 4,151,843 | 5/1979 | Brekke et al. ..................... 128/203 |
| 4,219,020 | 8/1980 | Czajka ............................ 128/207.13 |
| 4,312,339 | 1/1982 | Thompson, Sr. ................ 128/205.25 |
| 4,337,767 | 6/1982 | Yahata ............................ 128/206.28 |
| 4,794,921 | 1/1989 | Lindkvist ........................ 128/203.29 |
| 4,807,617 | 2/1989 | Nesti ................................ 128/205.12 |

FOREIGN PATENT DOCUMENTS

| | | | |
|---|---|---|---|
| 538809 | 11/1931 | Fed. Rep. of Germany ......................... 128/205.25 |
| 872634 | 8/1961 | United Kingdom .......... 128/205.25 |
| 2074457 | 11/1981 | United Kingdom .......... 128/206.21 |
| 2126904 | 4/1984 | United Kingdom .......... 128/205.25 |

OTHER PUBLICATIONS

Brochure published by MDT Corporation entitled The Reasons for Using the MDT/McKesson Scavenging Mask are Perfectly Clear.

*Primary Examiner*—Edgar S. Burr
*Assistant Examiner*—Eric P. Raciti
*Attorney, Agent, or Firm*—Jack M. Wiseman

[57] ABSTRACT

A mask for administering gas to a patient in which an inner cup-shaped wall fits over the nose of a patient and engages the face of the patient. An outer wall of the mask is detachably secured to and spaced from the inner wall to form an exhaust passage for the removal of gas exhaled by the patient. A floating disc valve is opened and closed by the exhaling and inhaling of the patient to control the flow of exhaust gas from the gas chamber of the inner wall to the exhaust passage. A valve seat of the floating disc valve is part of the inner wall and a flexible floating valve disc of the floating disc valve is attached to the valve seat. Formed in the peripheral edge of the inner wall is a recessed, V-shaped section to accommodate the middle of the nose and to form a seal against gas leakage.

25 Claims, 3 Drawing Sheets

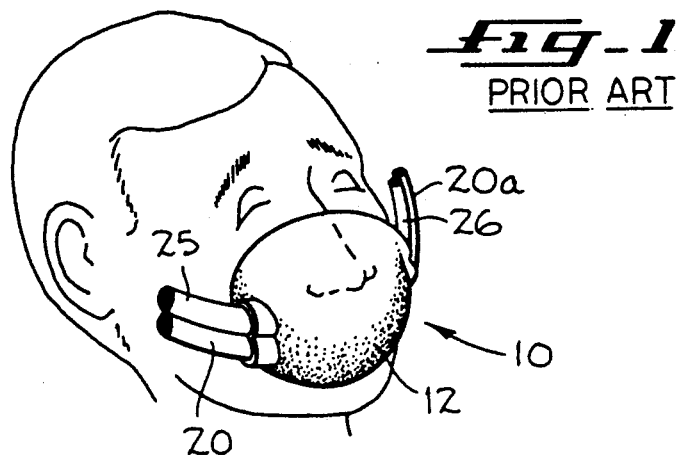
Fig_1
PRIOR ART
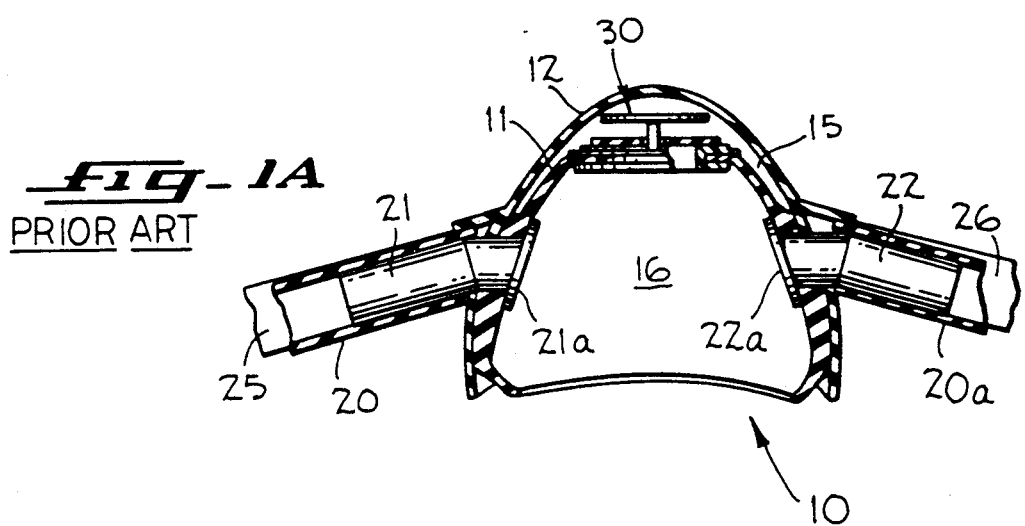
Fig_1A
PRIOR ART
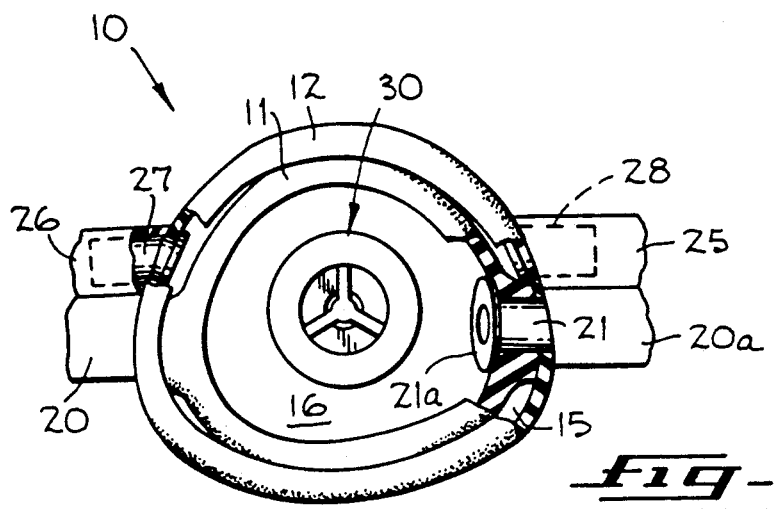
Fig_1B
PRIOR ART

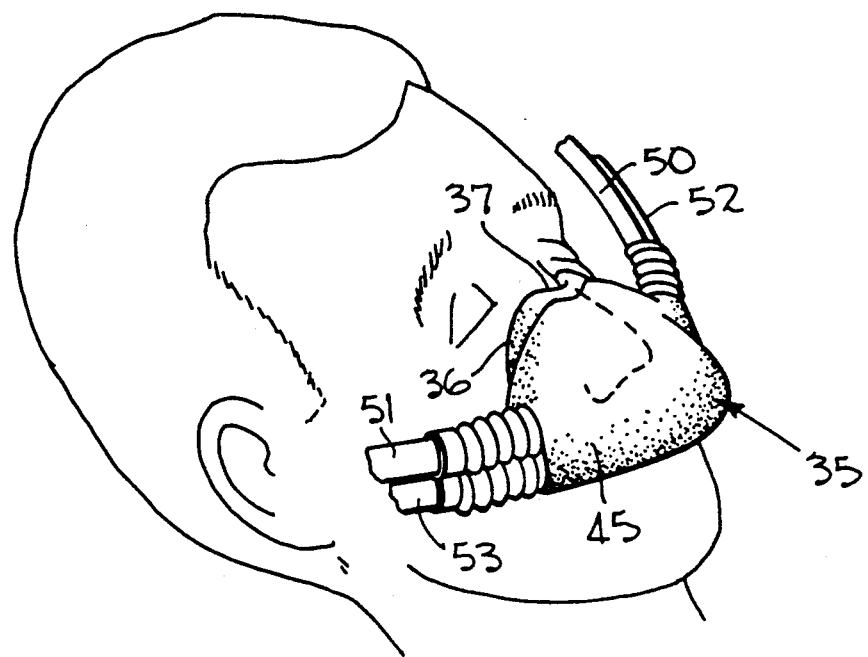
fig_2
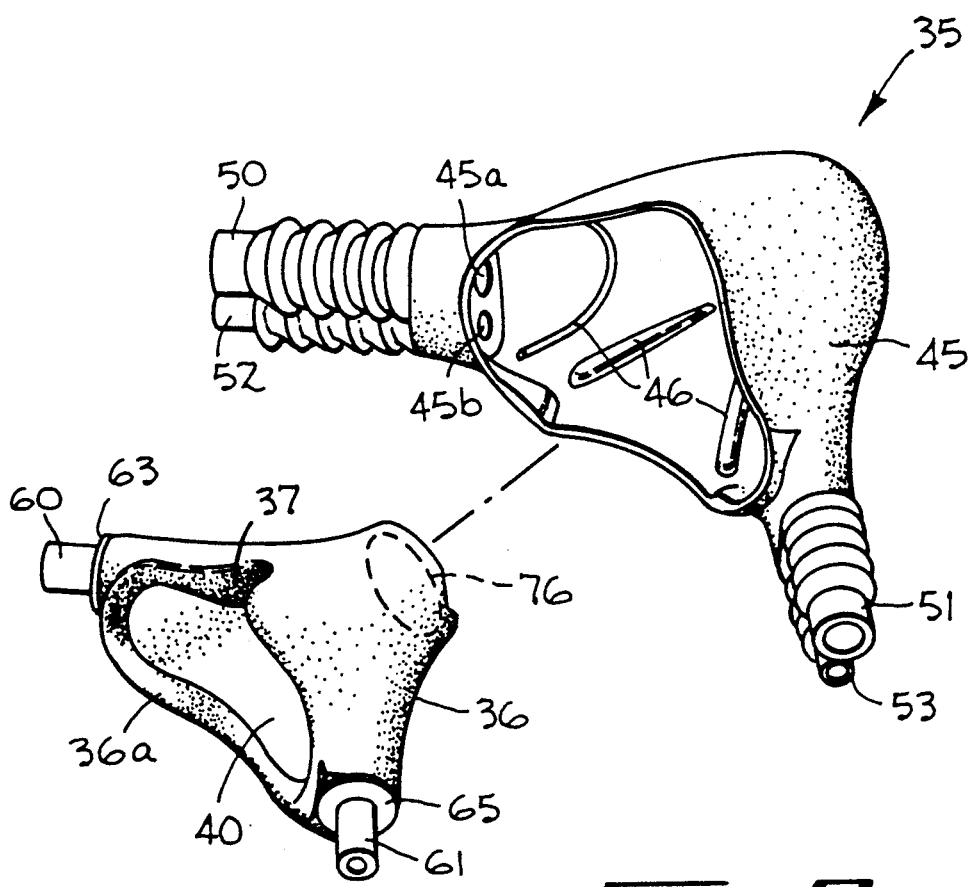
fig_3

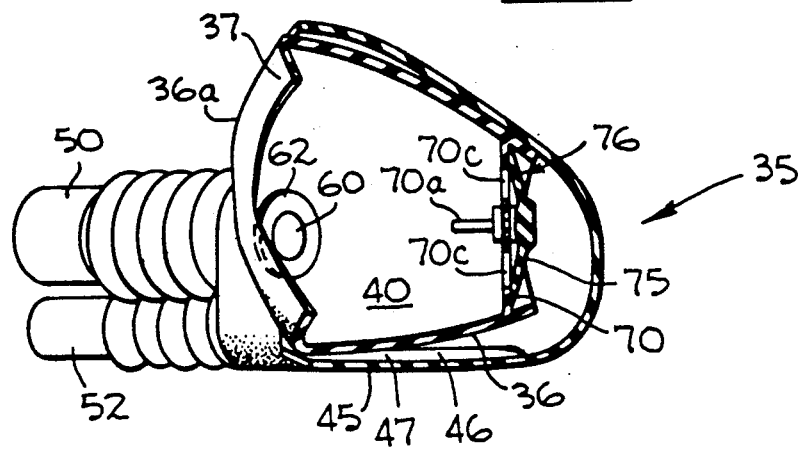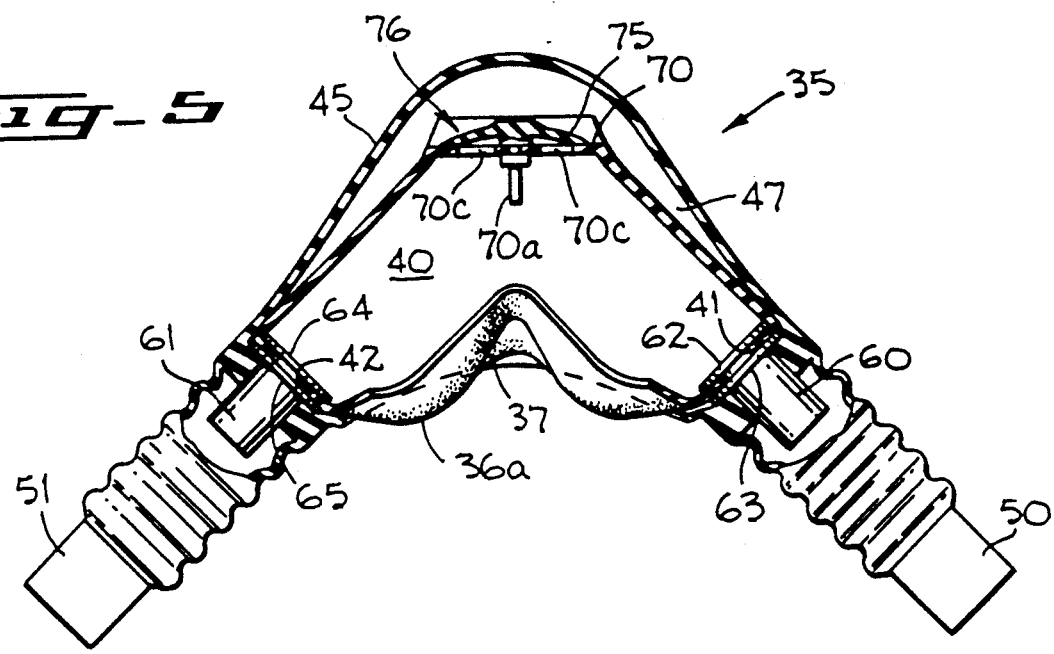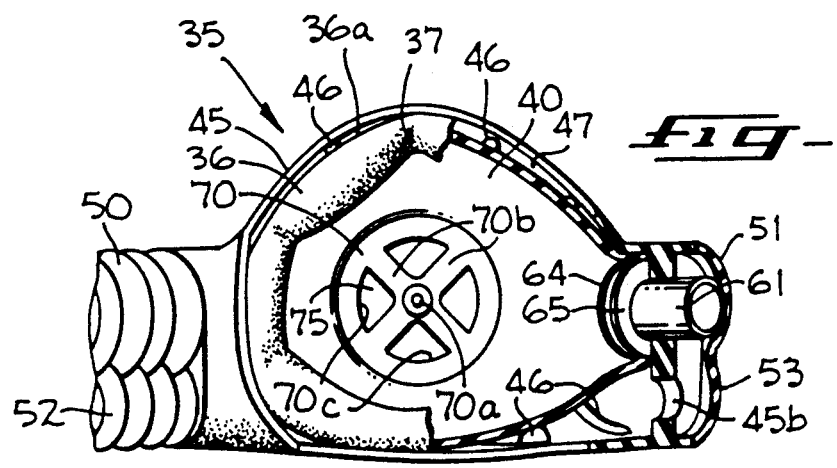

MASK FOR ADMINSTERING AN ANESTHETIC GAS TO A PATIENT

BACKGROUND OF THE INVENTION

The present invention relates in general to masks for the administering of anesthetic gas to a patient, and more particularly to a mask suitable for the administration of anesthetic gas to a dental patient.

Heretofore, it was the general practice for dentists to use the same mask on a plurality of patients for the administration of anesthetic gas. Such practices were of concern to the dentist, as well as the patient, because of the possibility of cross-contamination. In certain instances, the entire dental mask was intended for single patient use.

In the Glenn E. Brown U.S. Pat. No. 4,015,598, issued on Apr. 5, 1977, for Anaesthesic System, there is disclosed a mask for the administration of anesthetic gas to a dental patient. The mask comprises an inner cup-shaped wall to fit over the nose or the mouth of a patient. The inner wall engages the face of the patient along the peripheral edge of the inner cup to form a gas chamber between the face of the patient and the inner surface of the inner wall. An outer cup-shaped wall was secured to and spaced from the inner wall to form an exhaust passage between the inner and outer walls. The exhaust passage communicates with the gas chamber when the patient exhales. The peripheral edge of the outer wall is disposed in the vicinity of the peripheral edge of the inner wall to draw into the exhaust passage gas leaking between the face of the patient and the inner wall. Gas is introduced into the chamber to be inhaled by the patient. A valve is interposed between the inner and outer walls and is opened to permit exhaust gas to flow into the exhaust passage from the gas chamber when the patient exhales. When the patient inhales, the valve is closed blocking the passage of gas from the gas chamber to the exhaust passage.

The Czajka U.S. Pat. No. 4,219,020, issued on Aug. 26, 1980, for Scavenger Valve Attachment For Inhalation Sedation System Mask, discloses a scavenging attachment mounted on a face mask. An exhalation aperture leads through a floating disc check valve to a vacuum chamber which extends in a generally concave inverted saucer configuration over and around the mask. The vacuum chamber communicates with the surrounding atmosphere by means of an annular aperture in order to scavenge from the atmosphere adjacent the patient's face any gas escaping from the periphery of the mask.

MDT McKesson has sold a Twin-Trac Scavenging Mask having a disposable safety seal that was removably attached to the perimeter of the mask and engageable with the face of the patient. The tubing connecting the mask is adjustable by normal movement to accommodate patient position and movement. Additionally, the entire unit is heat and steam sterilizable including the tubing by well-known and conventional procedures.

In the Brekke et al. U.S. Pat. No. 4,151,843, granted on May 1, 1979, for Apparatus For Administration Of A Gas To A Human And The Exhausting Thereof, there is disclosed a mask for the administration of anesthetic gas to a patient in which the mask thereof is hollow and covers the entire nose. The mask terminates in two projections on its inner surface which engage the external portion of the nasal orifices bilaterally, thereby preventing leakage of gases out of or into the system at that point.

The Myers U.S. Pat. No. 3,721,239, issued on Mar. 20, 1973, for Anesthetic Gas Exhaust System, discloses an exhaust system for removal of anesthetic gas from an operating theatre. The manifold for the system has tubing attached thereto and is connected to the suction system. Attached to an end of the tubing is a corrugated hose which is flexible and which is corrugated in a bellow fashion.

The McKesson U.S. Pat. No. 1,632,449, issued on June 14, 1927, for a Mask, discloses a mask that fits over the nose of a patient for the administering of anesthetic gas. The mask includes an elastic flap that extends inwardly from the mask opening.

In the Bartlett, Jr. et al. U.S. Pat. No. 3,395,701, issued on Aug. 6, 1968, for End Tidal Sampler For An Oxygen Breathing Mask, there is disclosed a standard oxygen mask. The upper portion of the mask has an inwardly directed section that appears it may fit over the entire nose of the user.

Accutron of Phoenix, Arizona has manufactured and sold a dental mask with a valve. The single cup-shaped wall mask has a valve seat with openings formed therein as part of the single cup-shaped wall. The valve includes a valve disc that normally covers the openings by seating against the valve seat to close the valve. When the patient exhales, the valve disc is displaced from the valve seat to open the valve. The gas chamber of the dental mask communicates with an exhaust system through the opened valve. The valve disc is axially attached to the valve seat at the hub thereof.

SUMMARY OF THE INVENTION

A mask for administering gas to a patient in which an inner cup-shaped wall fits over the nose or mouth of a patient and engages the face of the patient. The inner wall forms a gas chamber. An outer wall of the mask is detachably secured to and spaced from the inner wall to form an exhaust passage for the removal of gas exhaled by the patient. Gas inlet means is supported by the outer wall and is detachably secured to the inner wall for introducing gas into the gas chamber to be inhaled by the patient. Exhaust gas outlet means is supported by the outer wall and communicates with the exhaust passage for removing exhaust gas from the exhaust passage. Interposed between the inner and outer walls is a floating valve disc made of a flexible rubber or plastic that forms a floating disc valve with a valve seat of the inner wall. When the patient inhales, the floating disc valve is closed to prevent communication between the gas chamber and the exhaust passage. When the patient exhales, the floating disc valve is opened for the exhaled gas to enter the exhaust passage.

An object of the present invention is to minimize cross-contamination that may be present in the use of a mask by a plurality of patients in the administration of anesthetic gas.

A feature of the present invention is the provision of a multiple wall mask in which the inner wall of the mask contacting the face of the patient and the valve are detachable from an outer wall of the mask with facility so as to be disposable while retaining the outer wall and its attachments for reuse.

Another feature of the present invention is the provision of a multiple wall mask in which the inner wall of the mask contacting the face of the patient and the valve are detachable from an outer wall of the mask with facility for sterilization while retaining the outer wall and its attachments for reuse.

Another feature of the present invention is the contour of an inner wall of a mask at a location at which the inner wall engages a center section of the nose of the patient to form a tight seal over the center of the nose while enabling the mask to be spaced from the eyes of the patient.

Another feature of the present invention is the floating valve disc is made of a soft flexible rubber or plastic and is interposed between the outer wall and the inner wall of the mask to control the flow of exhaled gas between the gas chamber and the exhaust passage.

DESCRIPTION OF THE DRAWINGS

FIG. 1 illustrates a mask of the prior art placed on a patient for administering an anesthetic gas.

FIG. 1A is a cross-sectional view of the mask of the prior art shown in FIG. 1.

FIG. 1B is a fragmentary bottom view partially in section of the mask of the prior art shown in FIGS. 1 and 1A.

FIG. 2 is an illustration of a mask embodying the present invention placed over the nose of a patient for administering an anesthetic gas.

FIG. 3 is an exploded view of the mask embodying the present invention shown in FIG. 2.

FIG. 4 is a fragmentary vertical sectional view partially in elevation of the mask embodying the present invention shown in FIGS. 2 and 3.

FIG. 5 is a cross-sectional view partially in elevation of the mask embodying the present invention shown in FIGS. 2–4.

FIG. 6 is a fragmentary bottom view partially in section of the mask embodying the present invention.

DESCRIPTION OF A PRIOR ART MASK

Illustrated in FIGS. 1, 1A and 1B is a prior art mask 10 comprising an inner wall 11 having a generally cup-shaped configuration. The inner wall 11 is made of a soft, flexible rubber or plastic and fits over the nose or mouth of a patient for the administration of gas. Secured to and spaced from the inner wall 11 is an outer wall 12 that forms with the inner wall 11 an exhaust passage 15 therebetween.

The perimeter of the inner wall 11 engages the face of the patient. The inner wall 11 forms a gas chamber 16 confronting the face of the patient. Inlet tubes 20 and 20a are supported by the outer wall 12. Disposed within the inlet tubes 20 and 20a are rigid plastic conduits 21 and 22 which communicate with the gas chamber 16 to introduce an anesthetic gas into the gas chamber 16 to be inhaled by the patient. At the end of the conduits 21 and 22 are flanges 21a and 22a, respectively, which abut against the inner surface of the inner wall 11. While the conduits 21 and 22 can be detached from the inner wall 11, it cannot be accomplished with facility.

Exhaust tubes 25 and 26 are supported by the outer wall 12. Within the exhaust tubes 25 and 26 are rigid exhaust conduits 27 and 28, respectively, which communicate with the exhaust passage 15. A source of vacuum draws exhaust gas from the exhaust passage 15. Supported by the inner wall 11 at the apex of the inner wall 11 and confronting the opening of the gas chamber 16 is a floating disc valve 30 made of rigid plastic material. The floating disc valve 30 is partially disposed between the inner wall 11 and the outer wall 12 for controlling the passage of exhaust gas between the gas chamber 16 and the exhaust passage 15. The entire floating disc valve 30 is separable from the inner wall 11 including the rigid valve seat with the openings therein.

When the patient inhales, the floating disc valve 30 closes the opening in the inner wall 11 between the gas chamber 16 and the exhaust passage 15. At that time, the patient inhales the anesthetic gas introduced into the gas chamber 16. When the patient exhales, the floating disc valve 30 opens the opening between the inner wall 11 and the exhaust passage 15 so that the exhaust gas is drawn from the gas chamber 16 into the exhaust passage 15 by the source of vacuum. The perimeter of the outer wall 12 is in the general vicinity of the perimeter of the inner wall 11. Any gas escaping from the mask 10 between the face of the patient and the mask 10 is scavenged into the exhaust passage 15 and removed therefrom by the source of vacuum.

DESCRIPTION OF THE PREFERRED EMBODIMENT

Illustrated in FIGS. 2–6 is a mask 35 embodying the present invention for administering anesthetic gas to a patient. In the exemplary embodiment, the mask 35 fits over the nose of the patient. Masks of this nature are adapted to fit over the mouth or nose of a patient.

The mask 35 comprises an inner cup-shaped wall 36 made of a soft, flexible rubber or plastic, such as silicone rubber. The perimeter 36a of inner wall 36 is folded over in the inward direction. When the mask 35 is placed over the nose of the patient, the perimeter 36a of the inner wall 36 engages the face of the patient. The perimeter 36a of the inner wall 36 serves to provide an improved seal between the inner wall 36 and the face of the patient. The inner wall 36 forms a gas chamber 40 confronting the face of the patient. In the exemplary embodiment, openings 41 and 42 are formed in the inner wall 36 for the introduction of anesthetic gas into the gas chamber 40. At the upper, central portion of the perimeter 36a of the inner wall 36 is formed an inwardly directed, generally V-shaped recessed area 37 to accommodate the center of the nose of the patient. The surfaces forming the generally V-shaped area 37 are directed toward the gas chamber 40 and form a tight seal over the center of the nose while enabling the mask 35 to maintain a spaced relation relative to the eyes of the patient. The configuration of the perimeter 36a forming the recessed area 37 is adaptable to conform to the shape of the center of the nose of the patient. The mask 35 is kept away from the eyes of the patient for safety reasons and still forms an effective seal between the inner wall 36 of the mask 35 and the face of the patient.

Supported by the inner wall 36 and spaced therefrom is an outer wall 45. The outer wall 45, in the exemplary embodiment, is made of flexible rubber or plastic, such as silicone rubber. Spacers or ribs 46 are formed on the outer wall and confront the inner wall 36 to maintain a spaced relation between the inner wall 36 and the outer wall 45. The space between the inner wall 36 and the outer wall 45 forms an exhaust passage 47. Openings 45a and 45b are formed in the outer wall 45 for exhaust gas to be removed from the exhaust passage 47 by a suitable source of vacuum, not shown.

In the exemplary embodiment, integrally formed with the outer wall 45 are gas inlet tubes 50 and 51. Integrally formed with the outer wall 45, in the exemplary embodiment, are exhaust tubes 52 and 53. The tubes 50–53 are made of flexible rubber or plastic with corrugated configurations for improved flexibility in positioning the hoses connected to the tubes 50-53.

Disposed within the gas inlet tubes 50 and 51 are rigid conduits 60 and 61, respectively. The rigid conduits 60 and 61 are made of a suitable rigid plastic and provide a tight fitting engagement with the interior walls of the associate tubes 50 and 51. The conduits 60 and 61 extend into the gas chamber 40 via the openings 41 and 42, respectively, of the inner wall 36. At the end of the conduit 60, that is received by the opening 41, are radially spaced annular flanges 62 and 63. The inner wall 36 is disposed between the flanges 62 and 63 in sealing engagement with the conduit 60 for anesthetic gas to be introduced into the gas chamber 40. The inlet tube 50 is disposed in a tight fitting sealing engagement with the conduit 60. By means of the double flanges 62 and 63 of the conduit 60, the inner wall 36 is removably secured to the conduit 60 and facilitates the removal of the inner wall 36 from the outer wall 45.

At the end of the conduit 61, that is received by the opening 42, are radially spaced annular flanges 64 and 65. The inner wall 36 is disposed between the flanges 64 and 65 in sealing engagement with the conduit 61 for anesthetic gas to be introduced into the gas chamber 40. The inlet tube 51 is disposed in a tight fitting sealing engagement with the conduit 61. By means of the double flanges 64 and 65 of the conduit 61, the inner wall 36 is removably secured to the conduit 61 and facilitates the removal of the inner wall 36 from the outer wall 45.

Integrally formed with the inner wall 36 is an annular valve seat 70 with a hub 70a, spokes 70b and sectors 70c in the form of openings. Disposed between the valve seat 70 of the inner wall 36 and the outer wall 45 is a floating valve disc 75. The valve seat 70 and the floating valve disc 75 form a floating disc valve 76. The floating disc valve 76 is made of a soft flexible rubber or plastic, such as silicone rubber. The floating valve disc 75 is secured to or otherwise caused to adhere to the hub 70a of the valve seat 70. The floating valve disc 75 is coextensive with the valve seat 70 and is interposed between the valve seat 70 and the outer wall 45.

Normally, the floating valve disc 75 is in sealing engagement with the valve seat 70 to close the opening sectors 70c by virtue of its securement to the hub 70a of the valve seat 70. When the floating valve disc 75 is in sealing engagement with the valve seat 70, the gas chamber 40 does not communicate with the exhaust passage 47 since the sectors 70c are closed. When the patient inhales, the floating valve disc 75 is in sealing engagement with the valve seat 70 and the opening sectors 70c are closed to prevent exhaust gas from entering the gas chamber 40 and to prevent anesthetic gas introduced into the gas chamber 40 from escaping into the exhaust passage 47. When the patient exhales, the floating valve disc 75 is radially displaced from the valve seat 70 and exhaust gas in the gas chamber 40 enters the exhaust passage 47 via the opening sectors 70c of the valve seat 70. A suitable source of vacuum, not shown, continuously removes exhaust gas from the exhaust passage 47 via the tubes 52 and 53.

In the exemplary embodiment, the perimeter of the outer wall 45 is disposed in the general vicinity of the perimeter 36a of the inner wall 36. In the event of leakage of anesthetic gas or exhaust gas between the inner wall 36 and the face of the patient, the source of vacuum draws the leaking gas into the exhaust passage 47 and removes the leaking gas from the exhaust passage 47 into the exhaust tubes 52 and 53.

By virtue of the present invention, the inner wall 36 with the floating disc valve 76 can be removed from the outer wall 45 with greater facility. The inner wall 36 with the floating disc valve 76 can be replaced by an unused inner wall 36 with a floating disc valve 76, or the inner wall 36 with the floating disc valve 76 can be removed and sterilized in a conventional manner for reuse.

What is claimed is:

1. A mask for administering gas to a patient comprising:
   (a) an inner cup-shaped wall having an inner surface and a peripheral edge, said inner wall being constructed and configured to fit over the nose or mouth of the patient and to engage the face of the patient along the peripheral edge thereof to form a gas chamber confronting the face of the patient, said inner wall being formed with a valve seat having at least one opening therein communicating with said gas chamber;
   (b) an outer wall detachably secured to said inner wall by a releasable securing means for facilitating the removal of said outer wall from said inner wall to enable said outer wall to be reused while discarding said inner wall, said outer wall being spaced from said inner wall to define an exhaust passage therebetween;
   (c) gas inlet means supported by said outer wall and including a conduit communicating with said gas chamber for introducing gas into said gas chamber to be administered to the patient, said conduit being detachably secured to said inner wall;
   (d) exhaust outlet means supported by said outer wall and communicating with said exhaust passage for the removal of exhaust gas from said exhaust passage; and
   (e) a flexible floating valve disc attached to said valve seat and arranged to form a sealing closure with said valve seat overlying said opening in said valve seat, said flexible floating valve disc being interposed between said valve seat and said outer wall, said floating valve disc forming a sealing closure with said valve seat over said opening in said valve seat in response to the patient inhaling to inhibit communication between said gas chamber and said exhaust passage, said floating valve disc being radially displaced from said opening in said valve seat for exhaust gas in said gas chamber to enter said exhaust passage in response to the patient exhaling.

2. A mask as claimed in claim 1 wherein said valve seat is an integral part of said inner wall.

3. A mask as claimed in claim 2 wherein said valve seat comprises a hub, spokes and a sector in the form of an opening, said floating valve disc having an axial center and said floating valve disc being secured to the hub of said valve seat at the axial center thereof.

4. A mask as claimed in claim 1 wherein said inner wall being made of a soft, flexible material for providing a seal between said inner wall and the face of a patient, and said floating valve disc being made of a soft, flexible material for providing sealing engagement with said valve seat.

5. A mask as claimed in claim 2 wherein said inner wall being made of a soft, flexible material for providing a seal between said inner wall and the face of the patient, and said floating valve disc being made of a soft, flexible material for providing sealing engagement with said valve seat.

6. A mask as claimed in claim 1 wherein said inner wall is formed with an opening therethrough communicating with said gas chamber, and wherein said conduit of said gas inlet means is received by said opening in said inner wall and is formed with annular flanges spaced apart in the axial direction of said conduit for receiving therebetween said inner wall, said releasable securing means comprising said annular flanges for detachably connecting said conduit to said inner wall.

7. A mask as claimed in claim 1 wherein said outer wall is formed with a peripheral edge disposed in the vicinity of the peripheral edge of said inner wall for scavenging gas leaking between the peripheral edge of said inner wall and the face of the patient into said exhaust passage.

8. A mask as claimed in claim 6 wherein said conduit is made of rigid material.

9. A mask for administering gas to a patient comprising:
(a) an inner cup-shaped wall having an inner surface and a peripheral edge, said inner wall being constructed and configured to fit over the nose or mount of the patient and to engage the face of the patient along the peripheral edge thereof to form a gas chamber confronting the face of the patient, said inner wall being formed with a valve seat having at least one opening therein communicating with said gas chamber;
(b) an outer wall detachably secured to said inner wall by a releasable securing means for facilitating the removal of said outer wall from said inner wall to enable said outer wall to be reused while discarding said inner wall, said outer wall being spaced from said inner wall to define an exhaust passage therebetween.
(c) gas inlet means supported by said outer wall and communicating with said gas chamber for introducing gas into said gas chamber to be administered to the patient, said gas inlet means being detachably secured to said inner wall;
(d) exhaust outlet means supported by said outer wall and communicating with said exhaust passage for the removal of exhaust gas from said exhaust passage; and
(e) a flexible floating valve disc attached to said valve seat and arranged to form a sealing closure with said valve seat overlying said opening in said valve seat, said flexible floating valve disc being interposed between said valve seat and said outer wall, said floating valve disc forming a sealing closure with said valve seat over said opening in said valve seat in response to the patient inhaling to inhibit communication between said gas chamber and said exhaust passage, said floating valve disc being radially displaced from said opening in said valve seat for exhaust gas in said gas chamber to enter said exhaust passage in response to the patient exhaling.

10. A mask as claimed in claim 9 wherein said valve seat is an integral part of said inner wall.

11. A mask as claimed in claim 10 wherein said valve seat comprises a hub, spokes and a sector in the form of an opening, said floating valve disc having an axial center and said floating valve disc being secured to the hub of said valve seat at the axial center thereof.

12. A mask as claimed in claim 9 wherein said inner wall being made of a soft, flexible material for providing a seal between said inner wall and the face of the patient, and said floating valve disc being made of a soft, flexible material for providing sealing engagement with said valve seat.

13. A mask as claimed in claim 10 wherein said inner wall being made of a soft, flexible material for providing a seal between said inner wall and the face of the patient, and said floating valve disc being made of a soft, flexible material for providing sealing engagement with said valve seat.

14. A mask as claimed in claim 9 wherein said outer wall is formed with a peripheral edge disposed in the vicinity of the peripheral edge of said inner wall for scavenging gas leaking between the peripheral edge of said inner wall and the face of the patient into said exhaust passage.

15. A mask as claimed in claim 9 wherein said inner wall is formed with an opening therethrough communicating with said gas chamber, and wherein said gas inlet means includes a conduit received by said opening in said inner wall and said conduit being formed with annular flanges spaced apart in the axial direction of said conduit for receiving therebetween said inner wall, said releasable securing means comprising said annular flanges for detachably connecting said conduit to said inner wall.

16. A mask for administering gas to a patient comprising:
(a) an inner cup-shaped wall having an inner surface and a peripheral edge, said inner wall being constructed and configured to fit over the nose of a patient and to engage the face of the patient along the peripheral edge thereof to form a gas chamber confronting the face of the patient, said peripheral edge of said inner wall being partially directed in the direction of said gas chamber and recessed in a generally V-shaped configuration toward said gas chamber to conform to the central section of the nose of the patient;
(b) an outer wall detachable secured to said inner wall by a releasable securing means for facilitating the removal of said outer wall from said inner wall to enable said outer wall to be reused while discarding said inner wall, said outer wall being spaced from said inner wall to define an exhaust passage therebetween;
(d) exhaust outlet means communicating with said exhaust passage for the removal of exhaust gas from said exhaust passage; and
(e) means interposed between said inner and outer walls for controlling the flow of exhaust gas from said gas chamber into said exhaust passage.

17. A mask as claimed in claim 16 wherein said peripheral edge is folded over to form a flange for engaging the face of the patient.

18. A mask as claimed in claim 17 wherein said outer wall is formed with a peripheral edge disposed in the vicinity of the peripheral edge of said inner wall for scavenging gas leaking between the peripheral edge of said inner wall and the face of the patient into said exhaust passage.

19. A mask for administering gas to a patient comprising:
(a) an inner cup-shaped wall having an inner surface and a peripheral edge, said inner wall being constructed and configured to fit over the nose or mount of the patient and to engage the face of the patient along the peripheral edge thereof to form a gas chamber confronting the face of the patient, said inner wall being formed with a valve seat having at least one opening therein communicating with said gas chamber;

(b) an outer wall detachably secured to said inner wall by a releasable securing means for facilitating the removal of said outer wall from said inner wall to enable said outer wall to be reused while discarding said inner wall, said outer wall being spaced from said inner wall to define an exhaust passage therebetween;

(c) gas inlet means supported by said outer wall and communicating with said gas chamber for introducing gas into said gas chamber to be administered to the patient;

(d) exhaust outlet means supported by said outer wall and communicating with said exhaust passage for the removal of exhaust gas from said exhaust passage; and (e) a flexible floating valve disc attached to said valve seat and arranged to form a sealing closure with said valve seat overlying said opening in said valve seat, said flexible floating valve disc being interposed between said valve seat and said outer wall, said floating valve disc forming a sealing closure with said valve seat over said opening in said valve seat in response to the patient inhaling to inhibit communication between said gas chamber and said exhaust passage, said floating valve disc being radially displaced from said opening in said valve seat for exhaust gas in said gas chamber to enter said exhaust passage in response to the patient exhaling.

20. A mask as claimed in claim 19 wherein said valve seat is an integral part of said inner wall.

21. A mask as claimed in claim 20 wherein said valve seat comprises a hub, spokes and a sector in the form of an opening, said floating valve disc having an axial center and said floating valve disc being secured to the hub of said valve seat at the axial center thereof.

22. A mask as claimed in claim 19 wherein said inner wall being made of a soft, flexible material for providing a seal between said inner wall and the face of the patient, and said floating valve disc being made of soft, flexible material for providing sealing engagement with said valve seat.

23. A mask as claimed in claim 19 wherein said inner wall being made of a soft, flexible material for providing a seal between said inner wall and the face of the patient, and said floating valve disc being made of soft, flexible material for providing sealing engagement with said valve seat.

24. A mask as claimed in claim 19 wherein said outer wall is formed with a peripheral edge disposed in the vicinity of the peripheral edge of said inner wall for scavenging gas leaking between the peripheral edge of said inner wall and the face of the patient into said exhaust passage.

25. A mask as claimed in claim 19 wherein said inner wall is formed with an opening therethrough communicating with said gas chamber, and wherein said gas inlet means includes a conduit received by said opening in said inner wall and said conduit being formed with annular flanges spaced apart in the axial direction of said conduit for receiving therebetween said inner wall, said releasable securing means comprising said annular flanges for detachably connecting said conduit to said inner wall.

* * * * *

REEXAMINATION CERTIFICATE (4216th)

United States Patent [19]
Brown

[11] B1 5,018,519
[45] Certificate Issued Nov. 28, 2000

[54] MASK FOR ADMINISTERING AN ANESTHETIC GAS TO A PATIENT

[75] Inventor: Glenn E. Brown, Soquel, Calif.

[73] Assignee: Porter Instrument Company, Inc., Hatfield, Pa.

Reexamination Request:
No. 90/005,319, Apr. 8, 1999

Reexamination Certificate for:
Patent No.: 5,018,519
Issued: May 28, 1991
Appl. No.: 07/562,242
Filed: Aug. 3, 1990

[51] Int. Cl.[7] .................................................. A61M 16/06
[52] U.S. Cl. ............................... 128/203.29; 128/205.25; 128/206.21; 128/206.28

[56] References Cited

U.S. PATENT DOCUMENTS

| | | |
|---|---|---|
| 823,946 | 6/1906 | Hill . |
| 2,848,994 | 8/1958 | Aguado . |
| 2,888,012 | 5/1959 | Larson . |
| 4,219,020 | 8/1980 | Czajka . |
| 4,265,239 | 5/1981 | Fischer, Jr. et al. . |
| 4,770,169 | 9/1988 | Schmoegner et al. . |

FOREIGN PATENT DOCUMENTS

| | | |
|---|---|---|
| 872684 | 8/1957 | United Kingdom . |

OTHER PUBLICATIONS

"N20" Scavenging Mask Installation and Usage Instructions" Narco McKesson, Sep. 1977.
"Dental Products Report" magazine, Jan. 1989 issue, p. 71 Personal Inhaler Plus.

*Primary Examiner*—John Weiss

[57] ABSTRACT

A mask for administering gas to a patient in which an inner cup-shaped wall fits over the nose of a patient and engages the face of the patient. An outer wall of the mask is detachably secured to and spaced from the inner wall to form an exhaust passage for the removal of gas exhaled by the patient. A floating disc valve is opened and closed by the exhaling and inhaling of the patient to control the flow of exhaust gas from the gas chamber of the inner wall to the exhaust passage. A valve seat of the floating disc valve is part of the inner wall and a flexible floating valve disc of the floating disc valve is attached to the valve seat. Formed in the peripheral edge of the inner wall is a recessed, V-shaped section to accommodate the middle of the nose and to form a seal against gas leakage.

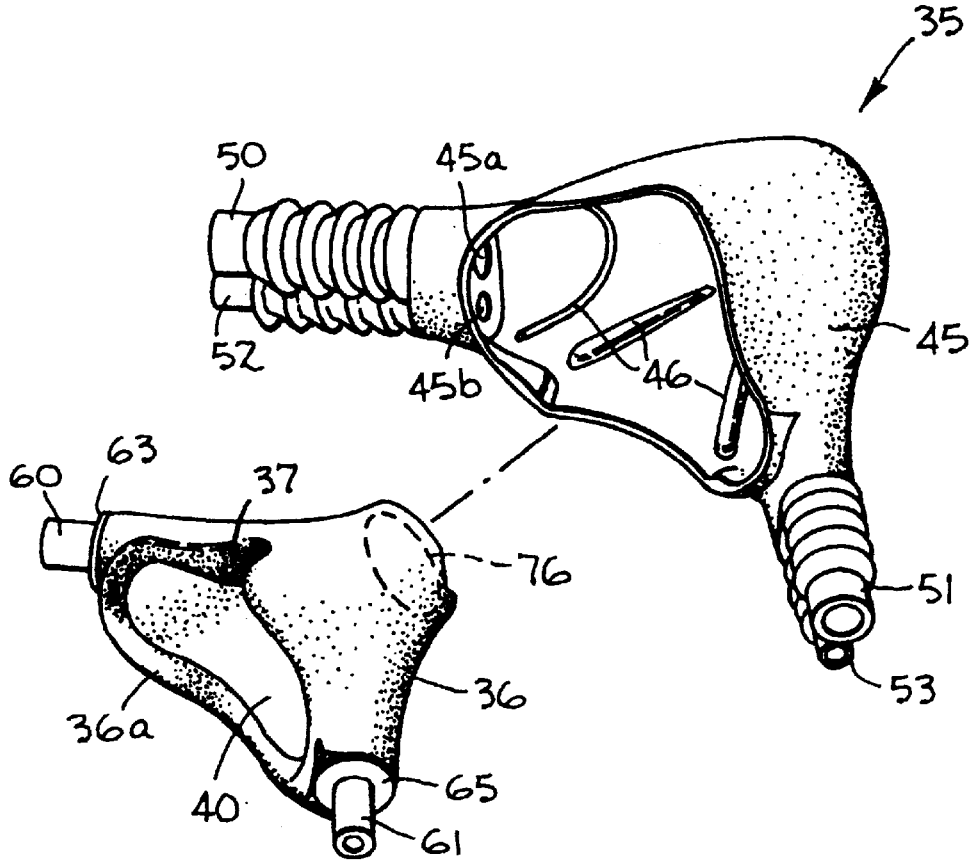

B1 5,018,519

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9, 16, 19 and 23 are determined to be patentable as amended.

Claims 2–8, 10–15, 17, 18, 20–22, 24 and 25, dependent on an amended claim, are determined to be patentable.

1. A mask for administering gas to a patient comprising:
   (a) an inner cup-shaped wall having an inner surface and a peripheral edge, said inner wall being constructed and configured to fit over the nose or mouth of the patient and to engage the face of the patient along the peripheral edge thereof to form a gas chamber confronting the face of the patient, said inner wall being formed with a valve seat having at least one opening therein communicating with said gas chamber;
   (b) an outer wall detachably secured to said inner wall by a releasable securing means for facilitating the removal of said outer wall from said inner wall to enable said outer wall to be reused while discarding said inner wall, said outer wall being spaced from said inner wall to define an exhaust passage therebetween *and said outer wall covering said valve seat*;
   (c) gas inlet means supported by said outer wall and including a conduit communicating with said gas chamber for introducing gas into said gas chamber to be administered to the patient, said conduit being detachably secured to said inner wall;
   (d) exhaust outlet means supported by said outer wall and communicating with said exhaust passage for the removal of exhaust gas from said exhaust passage; and
   (e) a flexible floating valve disc attached to said valve seat and arranged to form a sealing closure with said valve seat overlying said opening in said valve seat, said flexible floating valve disc being interposed between said valve seat and said outer wall, said floating valve disc forming a sealing closure with said valve seat over said opening in said valve seat in response to the patient inhaling to inhibit communication between said gas chamber and said exhaust passage, said floating valve disc being radially displaced from said opening in said valve seat for exhaust gas in said gas chamber to enter said exhaust passage in response to the patient exhaling.

9. A mask for administering gas to a patient comprising:
   (a) an inner cup-shaped wall having an inner surface and a peripheral edge, said inner wall being constructed and configured to fit over the nose or mou[nt]*th* of the patient and to engage the face of the patient along the peripheral edge thereof to form a gas chamber confronting the face of the patient, said inner wall being formed with a valve seat having at least one opening therein communicating with said gas chamber;
   (b) an outer wall detachably secured to said inner wall by a releasable securing means for facilitating the removal of said outer wall from said inner wall to enable said outer wall to be reused while discarding said inner wall, said outer wall being spaced from said inner wall to define an exhaust passage therebetween *and said outer wall covering said valve seat*.
   (c) gas inlet means supported by said outer wall and communicating with said gas chamber for introducing gas into said gas chamber to be administered to the patient, said gas inlet means being detachably secured to said inner wall;
   (d) exhaust outlet means supported by said outer wall and communicating with said exhaust passage for the removal of exhaust gas from said exhaust passage; and
   (e) a flexible floating valve disc attached to said valve seat and arranged to form a sealing closure with said valve seat overlying said opening in said valve seat, said flexible floating valve disc being interposed between said valve seat and said outer wall, said floating valve disc forming a sealing closure with said valve seat over said opening in said valve seat in response to the patient inhaling to inhibit communication between said gas chamber and said exhaust passage, said floating valve disc being radially displaced from said opening in said valve seat for exhaust gas in said gas chamber to enter said exhaust passage in response to the patient exhaling.

16. A mask for administering gas to a patient comprising:
    (a) an inner cup-shaped wall having an inner surface and a peripheral edge, said inner wall being constructed and configured to fit over the nose of a patient and to engage the face of the patient along the peripheral edge thereof to form a gas chamber confronting the face of the patient, said peripheral edge of said inner wall being partially directed in the direction of said gas chamber and recessed in a generally V-shaped configuration toward said gas chamber to conform to the central section of the nose of the patient;
    (b) an outer wall detachabl[e]*y* secured to said inner wall by a releasable securing means for facilitating the removal of said outer wall from said inner wall to enable said outer wall to be reused while discarding said inner wall, said outer wall being spaced from said inner wall to define an exhaust passage therebetween;
    (c) *gas inlet means communicating with said gas chamber for introducing gas into said gas chamber;*
    (d) exhaust outlet means communicating with said exhaust passage for the removal of exhaust gas from said exhaust passage; and
    (e) means interposed between said inner and outer walls for controlling the flow of exhaust gas from said gas chamber into said exhaust passage, *wherein said outer wall covers said means for controlling the flow of exhaust gas from said gas chamber into said exhaust passage.*

19. A mask for administering gas to a patient comprising:
    (a) an inner cup-shaped wall having an inner surface and a peripheral edge, said inner wall being constructed and configured to fit over the nose or mou[nt]*th* of the patient and to engage the face of the patient along the peripheral edge thereof to form a gas chamber confronting the face of the patient, said inner wall being formed with a valve seat having at least one opening therein communicating with said gas chamber;
    (b) an outer wall detachably secured to said inner wall by a releasable securing means for facilitating the removal of said outer wall from said inner wall to enable said outer wall to be reused while discarding said inner wall, said outer wall being spaced from said inner wall to define an exhaust passage therebetween *and said outer wall covering said valve seat*;

(c) gas inlet means supported by said outer wall and communicating with said gas chamber for introducing gas into said gas chamber to be administered to the patient;

(d) exhaust outlet means supported by said outer wall and communicating with said exhaust passage for the removal of exhaust gas from said exhaust passage; and (e) a flexible floating valve disc attached to said valve seat and arranged to form a sealing closure with said valve seat overlying said opening in said valve seat, said flexible floating valve disc being interposed between said valve seat and said outer wall, said floating valve disc forming a sealing closure with said valve seat over said opening in said valve seat in response to the patient inhaling to inhibit communication between said gas chamber and said exhaust passage, said floating valve disc being radially displaced from said opening in said valve seat for exhaust gas in said gas chamber to enter said exhaust passage in response to the patient exhaling.

23. A mask as claimed in claim [19] *20* wherein said inner wall being made of a soft, flexible material for providing a seal between said inner wall and the face of the patient, and said floating valve disc being made of soft, flexible material for providing sealing engagement with said valve seat.

\* \* \* \* \*